(12) United States Patent
Jang et al.

(10) Patent No.: US 11,585,796 B2
(45) Date of Patent: Feb. 21, 2023

(54) FLEXIBLE GRAPHENE GAS SENSOR, SENSOR ARRAY AND MANUFACTURING METHOD THEREOF

(71) Applicant: SEOUL NATIONAL UNIVERSITY R&DB FOUNDATION, Seoul (KR)

(72) Inventors: Ho Won Jang, Seoul (KR); Yeonhoo Kim, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 446 days.

(21) Appl. No.: 16/258,762

(22) Filed: Jan. 28, 2019

(65) Prior Publication Data
US 2020/0072807 A1    Mar. 5, 2020

(30) Foreign Application Priority Data

Aug. 29, 2018 (KR) .................. 10-2018-0101986

(51) Int. Cl.
| | | |
|---|---|---|
| B32B 38/10 | (2006.01) | |
| B32B 37/18 | (2006.01) | |
| B32B 37/24 | (2006.01) | |
| G01N 33/00 | (2006.01) | |
| C01B 32/182 | (2017.01) | |
| H01L 21/02 | (2006.01) | |

(52) U.S. Cl.
CPC ....... *G01N 33/0031* (2013.01); *B32B 37/182* (2013.01); *B32B 38/10* (2013.01); *C01B 32/182* (2017.08); *H01L 21/02527* (2013.01); *B32B 2037/243* (2013.01); *B32B 2037/246* (2013.01); *C01B 2204/22* (2013.01); *C01B 2204/24* (2013.01)

(58) Field of Classification Search
CPC ... B29C 66/84; B29C 65/7894; B29C 66/439; B29C 66/492; B29C 66/87; B29C 65/02; B31D 5/00; B31D 5/0073; B31D 2205/0082; B31D 2205/0023; B31D 2205/0047; G01N 33/0031
See application file for complete search history.

(56) References Cited

U.S. PATENT DOCUMENTS

| | | | |
|---|---|---|---|
| 2014/0130972 A1* | 5/2014 | Ren | B82Y 30/00 156/249 |
| 2015/0371848 A1* | 12/2015 | Zaretski | C23C 14/24 438/496 |
| 2016/0217888 A1* | 7/2016 | Xiang | E21B 17/003 |

FOREIGN PATENT DOCUMENTS

| | | | |
|---|---|---|---|
| KR | 10-1327501 | | 11/2013 |
| KR | 20140103015 A | * | 8/2014 |
| KR | 20150097145 A | * | 8/2015 |
| KR | 20160134975 A | * | 11/2016 |

OTHER PUBLICATIONS

KR20160134975A Machine Translation of Description (Year: 2021).*
KR20150097145A Machine Translation of Description (Year: 2021).*
KR20140103015A Machine Translation of Description (Year: 2021).*

(Continued)

*Primary Examiner* — Cynthia L Schaller

(57) ABSTRACT

The present invention relates to a surface-decorated flexible graphene self-heating gas sensor, which has a pattern of graphene formed on a flexible substrate, has a part of the pattern of graphene decorated with metal nanoparticles, and detects a gas by applying an external voltage.

16 Claims, 10 Drawing Sheets

(56) References Cited

OTHER PUBLICATIONS

Claramunt et al., "Flexible Gas Sensor Array With an Embedded Heater Based on Metal Decorated Carbon Nanofibres" (published Jan. 3, 2013) Elsevier B.V., Sensors and Actuators B 187 (2013) 401-406. (Year: 2013).*

Jimenez, I., Cirera, A., Folch, J., Cornet, A., and Morante, J.R., Innovative method of Pulverisation Coating of Pre-stabilized Nanopowders for Mass Production of Gas Sensors, Sensors and Actuators B 78 (2001), pp. 78-82. (Year: 2001).*

\* cited by examiner

FLEXIBLE GRAPHENE GAS SENSOR, SENSOR ARRAY AND MANUFACTURING METHOD THEREOF

CROSS-REFERENCE TO RELATED APPLICATION

This application claims priority of Korean Patent Application No. 10-2018-0101986, filed on Aug. 29, 2018, in the KIPO (Korean Intellectual Property Office), the disclosure of which is incorporated herein entirely by reference.

BACKGROUND OF THE INVENTION

Field of the Invention

The present disclosure relates to a flexible graphene gas sensor, a sensor array and a method for manufacturing the same, more particularly to a self-heating gas sensor manufactured by micro- or nano-patterning and surface decoration of graphene formed on a flexible substrate, a sensor array thereof and a method for manufacturing the same.

Description of the Related Art

Recently, as the interests in wearable devices, etc. utilizing flexible devices are increasing, two-dimensional materials are researched actively. The two-dimensional material refers to a material with a size of several nanometers (nm) in which small atoms are arranged in a single layer. Graphene is a typical example.

In general, graphite is a structure in which layers of carbon atoms arranged in a honeycomb lattice are stacked. The individual layers are called graphene. Graphene, which has a thickness of 0.2 nm, has high physical and chemical stability, conducts electricity 100 times or higher than copper, and exhibits electron mobility 100 times or faster than silicon. Also, it is transparent and has excellent flexibility. Therefore, researches are being carried out actively for the manufacturing and application thereof.

Graphene is reduced from graphene oxide by chemical exfoliation, mechanical exfoliation, epitaxial growth, chemical vapor deposition, high-temperature thermal annealing, etc. A single- or double-layered reduced graphene oxide (rGO) thin film exhibits the physical properties of a semiconductor and has low sheet resistance and high transparency. Some rGO thin films may be used as a structural element for improving the responsivity of a biosensor using their semiconductor properties.

Meanwhile, a gas sensor used for gas detection, etc. has been used in wide applications including chemistry, pharmaceutical, environment, medicine, etc. In particular, as the interests in the Internet of things, flexible devices, wearable devices, etc. are increasing and as higher performance is required for gas sensors, researches on gas sensors using two-dimensional materials are increasing rapidly.

However, the existing metal oxide gas sensor is disadvantageous in that it requires use of an external heater, lacks flexibility and is opaque. In addition, the recently emerging graphene-based gas sensor has the problem that it exhibits relatively low sensitivity as a gas sensor and exhibits unsatisfactory selectivity for specific gases.

SUMMARY OF THE INVENTION

The present disclosure is designed to solve the above-described problems of the related art and is directed to providing a self-heating transparent gas sensor with increased selectivity for specific gases through micro- or nano-patterning and surface decoration of graphene, a gas sensor array thereof and a method for manufacturing the same.

In an aspect, the present disclosure provides a surface-decorated flexible graphene self-heating gas sensor, which has a pattern of graphene formed on a flexible substrate, has a part of the pattern of graphene decorated with metal nanoparticles, and detects a gas by applying an external voltage.

In an exemplary embodiment of the present disclosure, the pattern of graphene may be micro- or nano-patterned such that a pair of graphenes in triangular shape are arranged in parallel and the graphenes arranged in parallel are connected by a graphene with a small width.

In an exemplary embodiment of the present disclosure, the metal nanoparticle may be one selected from gold (Au), platinum (Pt), silver (Ag), tin (Sn), indium (In), nickel (Ni), copper (Cu), cobalt (Co) and chromium (Cr).

In an exemplary embodiment of the present disclosure, the flexible substrate may be formed of a transparent material selected from a group consisting of polyimide (PI), acryl, polycarbonate, polyethylene terephthalate (PET) and polyethersulfone (PES).

In another aspect, the present disclosure provides a flexible graphene self-heating gas sensor array, which has a plurality of patterns of graphene are formed on a flexible substrate, has a part of each of the plurality of patterns of graphene decorated with metal nanoparticles, and detects a gas by applying an external voltage.

In an exemplary embodiment of the present disclosure, each of the plurality of patterns of graphene may be micro- or nano-patterned such that a pair of graphenes in triangular shape are arranged in parallel and the graphenes arranged in parallel are connected by a graphene with a small width.

In an exemplary embodiment of the present disclosure, the metal nanoparticles decorating each of the plurality of patterns of graphene may be different metal nanoparticles.

In an exemplary embodiment of the present disclosure, the flexible graphene self-heating gas sensor array may further contain a graphene pattern with no surface decoration on the flexible substrate, wherein the metal nanoparticles decorating each of the plurality of patterns of graphene include two or more selected from gold (Au), platinum (Pt), silver (Ag), tin (Sn), indium (In), nickel (Ni), copper (Cu), cobalt (Co) and chromium (Cr).

In another aspect, the present disclosure provides a method for manufacturing a surface-decorated flexible graphene self-heating gas sensor array, which includes a step of forming a graphene layer on a substrate, a step of forming a pattern of the graphene, a step of coating a flexible substrate solution on the patterned graphene layer and curing the same, a step of removing the substrate, and a step of decorating a part of the patterned graphene with metal nanoparticles.

In an exemplary embodiment of the present disclosure, the step of forming the pattern of the graphene may include a step of forming a micro- or nano-pattern such that a pair of graphenes in triangular shape are arranged in parallel and the graphenes arranged in parallel are connected by a graphene with a small width through a photolithography or e-beam lithography process.

In an exemplary embodiment of the present disclosure, the substrate may be a metal substrate containing a transition metal.

In an exemplary embodiment of the present disclosure, the substrate may be a metal substrate containing copper or nickel.

In an exemplary embodiment of the present disclosure, the step of removing the substrate may include a step of removing the metal substrate containing copper or nickel with ammonium persulfate, an aqueous $FeCl_3$ solution or a strong acid.

In an exemplary embodiment of the present disclosure, the method may further include a thermal lamination step after the coating and curing of the flexible substrate.

In an exemplary embodiment of the present disclosure, the step of decorating with the metal nanoparticles may include a step of depositing one or more metal nanoparticle(s) using an e-beam evaporator.

In an exemplary embodiment of the present disclosure, the metal nanoparticle may be one or more selected from gold (Au), platinum (Pt), silver (Ag), tin (Sn), indium (In), nickel (Ni), copper (Cu), cobalt (Co) and chromium (Cr).

In an exemplary embodiment of the present disclosure, the flexible substrate may be formed of a transparent material selected from a group consisting of polyimide, acryl, polycarbonate, polyethylene terephthalate and polyethersulfone.

The technology according to various exemplary embodiments of the present disclosure allows manufacturing of a flexible self-heating gas sensor with improved gas-sensing reactivity and selectivity through formation of a graphene pattern on a flexible substrate without an additional electrode and surface decoration. In addition, a gas sensor array capable of selectively sensing various gases may be formed through formation of a plurality of patterns on a flexible substrate and different surface decoration. Through this, a gas sensor can be manufactured economically without an external heater and the transparent and flexible gas sensor or gas sensor array can be utilized for Internet of things, smart sensors, wearable devices, mobile devices, etc.

The effects that can be achieved with the present disclosure is not limited to those described above and other additional effects not described above will be clearly understood by those having ordinary skill in the related art to which the present disclosure belongs from the following description.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

Figure 1:
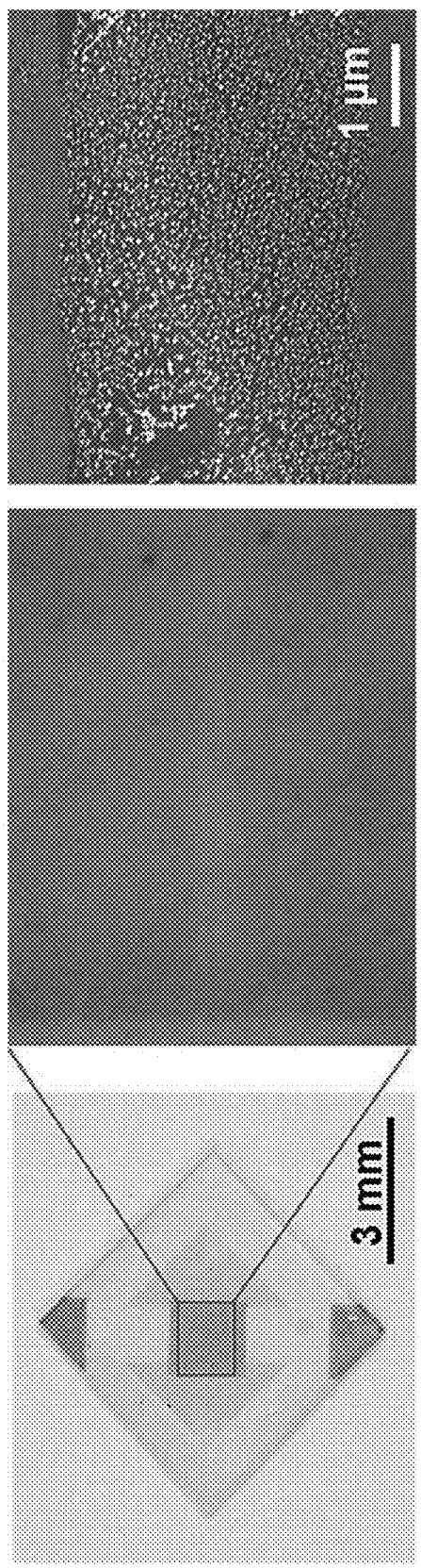
FIG. 1 schematically shows a surface-decorated graphene gas sensor according to an exemplary embodiment of the present disclosure.

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

Reference herein to a layer formed "on" a substrate or other layer refers to a layer formed directly on top of the substrate or other layer or to an intermediate layer or intermediate layers formed on the substrate or other layer. It will also be understood by those skilled in the art that structures or shapes that are "adjacent" to other structures or shapes may have portions that overlap or are disposed below the adjacent features.

In this specification, the relative terms, such as "below", "above", "upper", "lower", "horizontal", and "vertical", may be used to describe the relationship of one component, layer, or region to another component, layer, or region, as shown in the accompanying drawings. It is to be understood that these terms are intended to encompass not only the directions indicated in the figures, but also the other directions of the elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Figure 4:
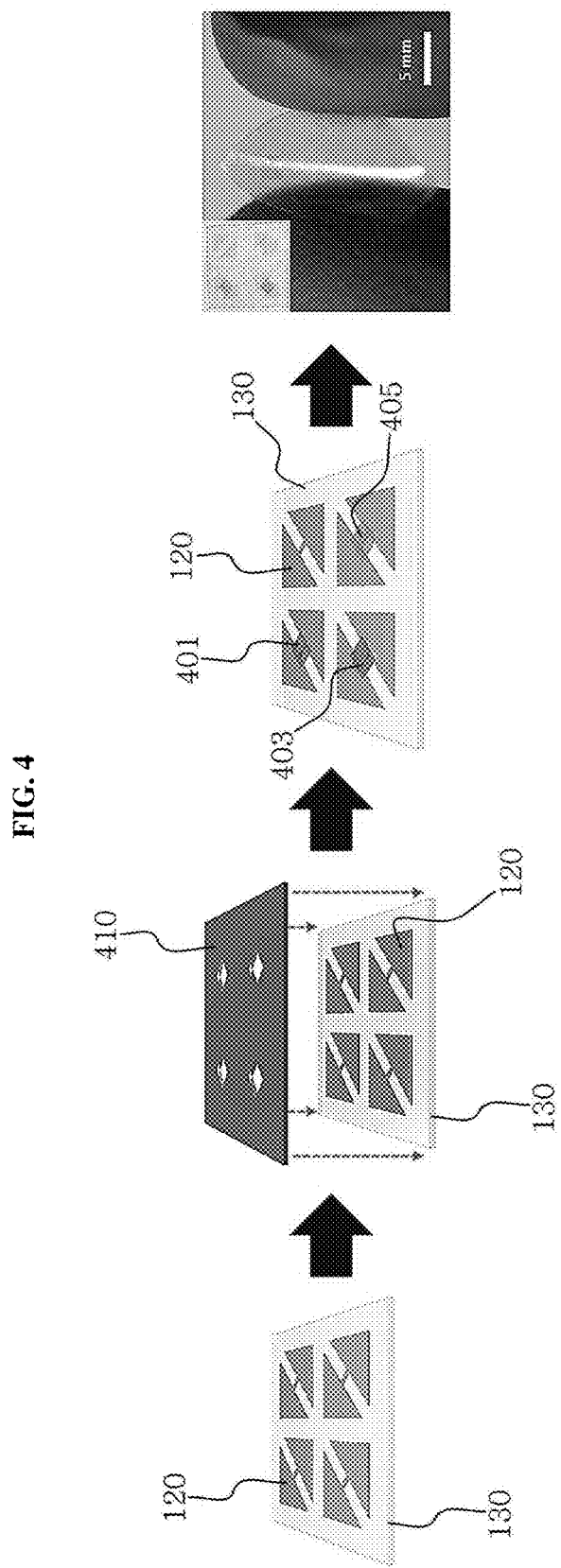
FIG. 4 illustrates the steps of a method for manufacturing a flexible sensor array through surface decoration according to an exemplary embodiment of the present disclosure.

The present disclosure relates to a flexible graphene gas sensor, a sensor array and a method for manufacturing the same. As shown in FIG. 4, it relates to a method for manufacturing a graphene gas sensor and a sensor array with different surface decorations.

Hereinafter, specific exemplary embodiments of the present disclosure are described referring to the attached drawings. Although the present disclosure is described referring to the exemplary embodiments illustrated in the drawings, they are provided only as specific examples and the technical idea and scope of the present disclosure are not limited by them.

FIG. 1 schematically shows a surface-decorated graphene gas sensor according to an exemplary embodiment of the present disclosure.

Referring to FIG. 1, the flexible graphene transparent gas sensor according to the present disclosure is formed of graphene only without an additional electrode. Through this, a flexible graphene gas sensor capable of self-heating may be provided. As shown in FIG. 1, a pair of graphenes in triangular shape are arranged in parallel and the graphenes arranged in parallel are connected by a graphene with a small width. For example, the patterning may be performed such that the width of the connected region is 3-5 μm or several nanometers. In addition, surface-decorated graphene may be formed by decorating the connected region with gold (Au) nanoparticles. Although gold (Au) as bulk metal is well known to have the lowest reactivity for atoms or molecules, gold (Au) nanoparticles smaller than 10 nm show great potential in applications such as selective oxidation and hydrogenation due to their catalytic activity. For the surface decoration, the gold (Au) nanoparticles may be deposited on the flexible substrate on which graphene is micro- or nano-patterned by chemical doping, plasma CVD (chemical vapor deposition) or PVD (physical vapor deposition) (e.g., e-beam deposition, sputtering, etc.). Besides, metal particles prepared by other chemical methods may be coated for the surface decoration. Although the surface decoration with gold (Au) nanoparticles is illustrated in the figure, various metal particles such as platinum (Pt), silver (Ag), tin (Sn), indium (In), nickel (Ni), copper (Cu), cobalt (Co), chromium (Cr), etc. can be used for the decoration without limitation.

Figure 2:
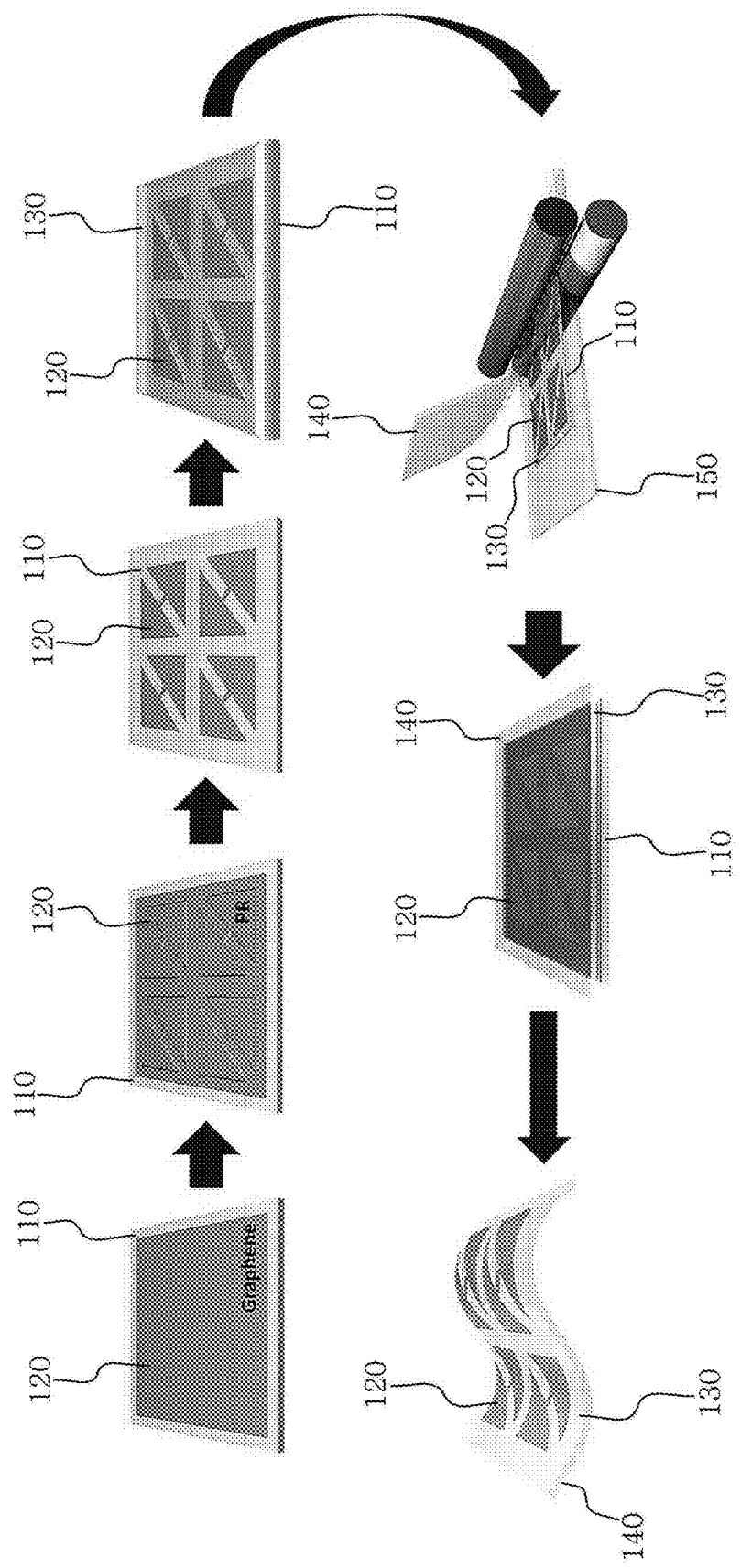
FIG. 2 illustrates the steps of a method for manufacturing a flexible device having a graphene micro-pattern or nano-pattern formed according to an exemplary embodiment of the present disclosure.

FIG. 2 illustrates the steps of a method for manufacturing a flexible device having a graphene micro-pattern or nano-pattern formed according to an exemplary embodiment of the present disclosure.

Specifically, referring to FIG. 2, a method for manufacturing a flexible sensor or a sensor array having a graphene pattern formed according to an exemplary embodiment of the present disclosure includes a step of forming graphene on a substrate, a step of forming a micro- or nano-pattern of the graphene, a step of coating and curing a target substrate solution, a step of thermally laminating a supporting substrate, a step of detaching or etching the substrate and a step of completing a flexible device having a graphene pattern formed thereon.

First, graphene 120 is formed on a substrate 110. In an exemplary embodiment of the present disclosure, the substrate 110 may be a transition metal thin film such as copper (Cu) and nickel (Ni) or a silicon (Si)- or silica ($SiO_2$)-based substrate. When considering the characteristics of the manufacturing process of the flexible device according to the present disclosure, the substrate 110 is not necessarily limited to a metal thin film or a hard substrate and any type of substrate may be used if a two-dimensional material can be patterned on the substrate. For example, graphene may be grown directly on a copper foil substrate 110 and, in this case, a chemical vapor deposition (CVD) method may be used.

Next, a pattern of the graphene 120 is formed on the substrate 110. As shown in FIG. 2, the graphene 120 formed on the substrate 110 may be patterned into a desired shape. For example, the graphene 120 may be patterned by a common photolithography or e-beam lithography process or may be elaborately micro- or nano-patterned. For a flexible substrate, it is difficult to pattern the graphene after transferring due to its material characteristics and micro- or nano-patterning is almost impossible. Therefore, a flexible substrate having graphene of a desired pattern formed thereon may be obtained by patterning (e.g., micro- or nano-patterning) the graphene 120 grown directly on the substrate 110 and then transferring the patterned graphene 120 to a flexible substrate 130. As shown in FIG. 2, a pair of graphenes in triangular shape are arranged in parallel and the graphenes arranged in parallel are connected by a graphene with a small width. For example, the patterning may be performed such that the width of the connected region is 3-5 μm or several nanometers. The shape of the graphene pattern is not limited to that shown in FIG. 2 and micro- or nano-patterns of various shapes may be formed.

Subsequently, a target substrate solution is coated and cured. That is to say, a flexible substrate (target substrate) solution is coated on the graphene 120 patterned on the substrate 110 and then cured to form a flexible substrate 130 on the patterned graphene 120. The flexible substrate may be formed of a flexible polymer material and may have a transparent property. The polymer constituting the flexible substrate is not limited. For example, the flexible substrate may be one selected from a group consisting of polyimide (PI), acryl, polycarbonate, polyvinyl alcohol, polyacrylate, polyethylene naphthalate (PEN), polyethylene terephthalate (PET), polynorbornene and polyethersulfone (PES).

Next, a thermal lamination process is conducted after the formation of the flexible substrate 130. The thermal lamination process is conducted by placing the flexible substrate 130 on which the patterned graphene 120 has been coated and cured on a supporting substrate 150 for thermal lamination and then laminating a thermal lamination film 140 thereon using a thermal laminator. The thermal lamination process may be conducted to ensure the stability of the substrate, if necessary, and may also be omitted.

Subsequently, the substrate 110 is removed by detaching or etching the same. As seen from FIG. 2, the substrate layer 110 is removed while retaining the cured flexible substrate 130 and the patterned graphene layer 120 through a detachment or etching process. For example, a copper (Cu) thin film substrate 110 may be etched using an ammonium persulfate (APS) solution, a FeCl3 solution, etc. and a nickel (Ni) substrate 110 may be removed with a strong acid such as HNO3, etc.

Finally, a flexible device is completed using the flexible substrate 130 having the pattern of graphene 120 formed. For example, a surface decoration process may be further conducted to complete a flexible sensor or a sensor array, as will be described later referring to FIG. 4. Although sensitivity for gases can be improved only with the graphene patterning, it is possible to control the selectivity and sensitivity for specific gases through different surface decorations. Through this method, a micro- or nano-patterned flexible device can be manufactured despite the material characteristics of the flexible substrate 130.

Figure 3:
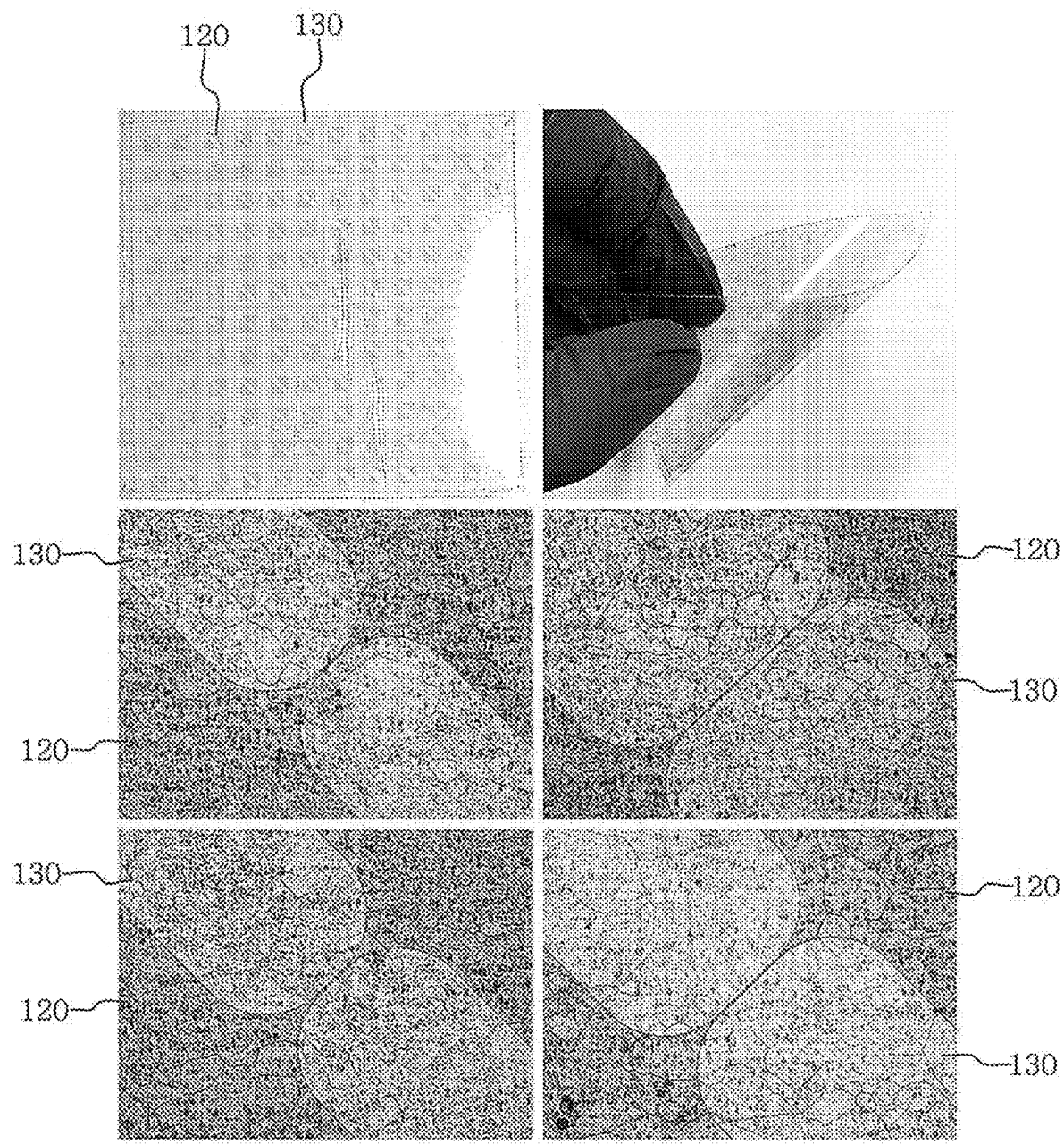
FIG. 3 shows a graphene micro- or nano-pattern formed on a flexible substrate according to an exemplary embodiment of the present disclosure.

FIG. 3 shows a micro- or nano-pattern of graphene 120 formed on a flexible substrate 130 according to an exemplary embodiment of the present disclosure.

FIG. 3 shows the images of patterned graphene 120 transferred to the flexible substrate 130. In FIG. 3, the images in the second and third rows are the magnified images of the connected region between the triangularly patterned graphenes 120 parallel to the flexible substrate 130. The patterning may be conducted such that the connected region is very thin. For example, the patterning may be performed such that the width of the connected region is 3-5 μm or several nanometers, as shown in FIG. 3. As the connected region is thinner and as the spacing between the triangularly patterned graphenes 120 is narrower, self-heating may be more efficient.

FIG. 4 illustrates the steps of a method for manufacturing a flexible sensor array through surface decoration according to an exemplary embodiment of the present disclosure.

Specifically, referring to FIG. 4, the method for manufacturing a flexible sensor array through surface decoration according to an exemplary embodiment of the present disclosure includes a step of placing a mask 410 on a flexible substrate having a plurality of graphene patterns formed thereon, a step of performing surface decoration 401, 403, 405 using the mask 410, and a step of completing a flexible sensor array having a graphene pattern with the surface decoration 401, 403, 405.

First, a mask 410 is placed on a flexible substrate 130 having a plurality of graphene patterns 120 formed thereon according to the procedure described referring to FIG. 2. In an exemplary embodiment of the present disclosure, the mask 410 may have a masking pattern with the number and positions determined according to the graphene pattern to be surface-decorated. Although the flexible sensor array shown in the example contains four gas sensors, one graphene pattern with no surface decoration and three graphene patterns with three different surface decorations, the number of the sensors of the sensor array, surface decoration, array type, etc. may be changed variously as desired without being limited thereto. Also, a single flexible graphene sensor can be manufactured.

Next, surface decoration 401, 403, 405 is performed using the mask 410. In an exemplary embodiment of the present disclosure, the surface decoration 401, 403, 405 can be performed by deposition by chemical doping, plasma CVD (chemical vapor deposition) or PVD (physical vapor deposition) (e.g., e-beam deposition, sputtering, etc.). Besides, metal particles prepared by other chemical methods may be coated for the surface decoration. In an exemplary embodiment of the present disclosure, the surface decoration (401) may be platinum (Pt), the surface decoration 2 (403) may be gold (Au), and the surface decoration 3 (405) may be silver (Ag). In addition, various metal particles such as tin (Sn), indium (In), nickel (Ni), copper (Cu), cobalt (Co), chromium (Cr), etc. may be used for the surface decoration without limitation. Although the flexible sensor array shown in FIG. 4 contains one graphene pattern with no surface decoration and three surface-decorated patterns, the number of the sensors of the sensor array, surface decoration, array type, etc. may be changed variously as desired without being limited thereto. Also, a single flexible graphene sensor can be manufactured.

Finally, a flexible sensor array having a graphene pattern with the surface decoration 401, 403, 405 is completed. The completed flexible sensor array may be transparent and flexible throughout the sensor array depending on the type of the flexible substrate and may have improved gas-sensing reactivity and selectivity, as will be described later.

Example 1: Manufacturing of Single Flexible Graphene Gas Sensor

Graphene was formed on copper (Cu) foil (purity 99.99%) by thermal chemical vapor deposition at 1000° C. by supplying a hydrocarbon ($CH_4$) at 30 sccm and hydrogen ($H_2$) at 5 sccm. After patterning the graphene by lithography, and conducting reactive ion etching (RIE), the patterned graphene was immersed in acetone. Subsequently, after coating a polyimide (PI) substrate solution on the patterned graphene, a thermal lamination film was laminated thereon by a thermal lamination process. Then, a graphene-patterned flexible substrate was completed by removing the copper (Cu) foil with an APS solution. A gold (Au) surface-decorated flexible graphene gas sensor was manufactured by separating the flexible substrate to contain only one graphene pattern and then depositing gold (Au) nanoparticles using an e-beam evaporator.

Example 2: Manufacturing of Flexible Graphene Gas Sensor Array

A graphene-patterned flexible substrate was completed in the same manner as in Example 1. Four graphene patterns were formed on the flexible substrate. A graphene gas sensor array surface-decorated with platinum (Pt), gold (Au) and silver (Ag) was manufactured by depositing platinum (Pt), gold (Au) and silver (Ag) nanoparticles, respectively, on three of the four graphene patterns, with one of them leaving not surface-decorated.

Figure 5A:
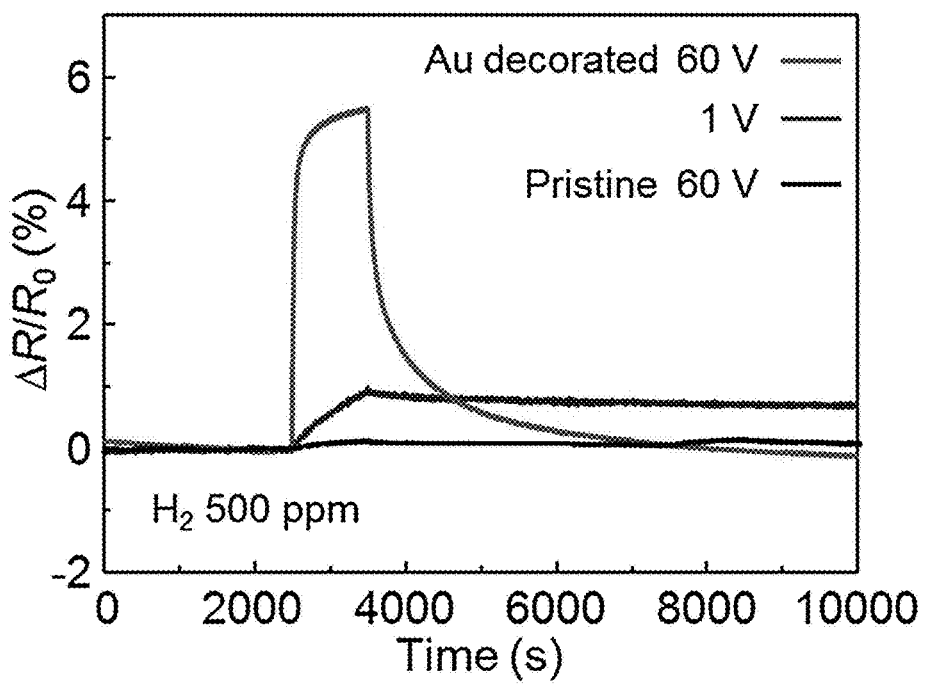
FIGS. 5A and 5B show the change of the H2 gas-sensing characteristics and temperature of a surface-decorated graphene gas sensor according to an exemplary embodiment of the present disclosure.
Figure 5B:
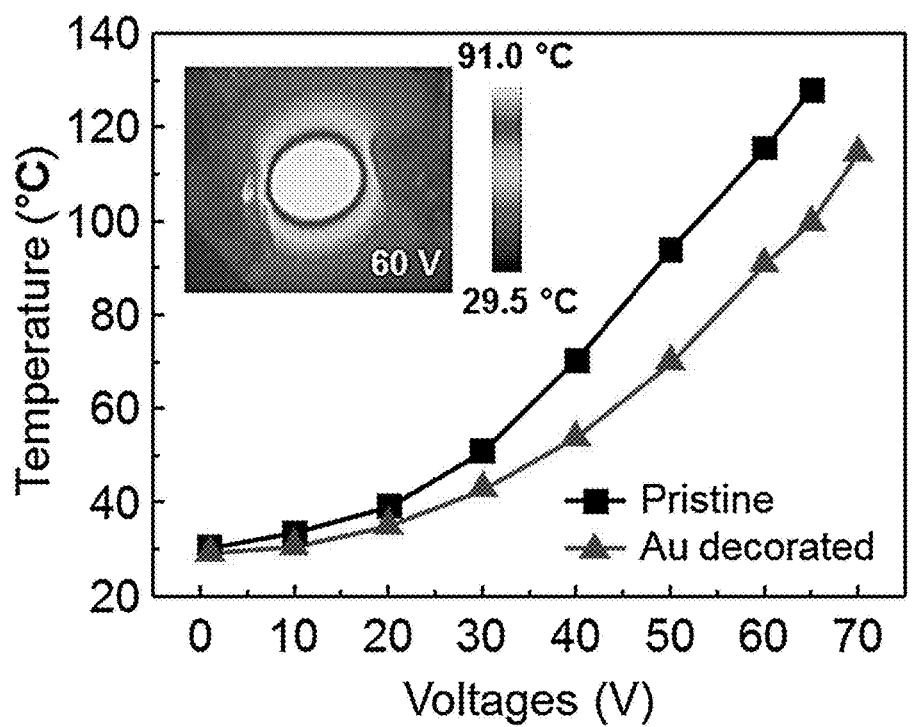
Figure 6A:
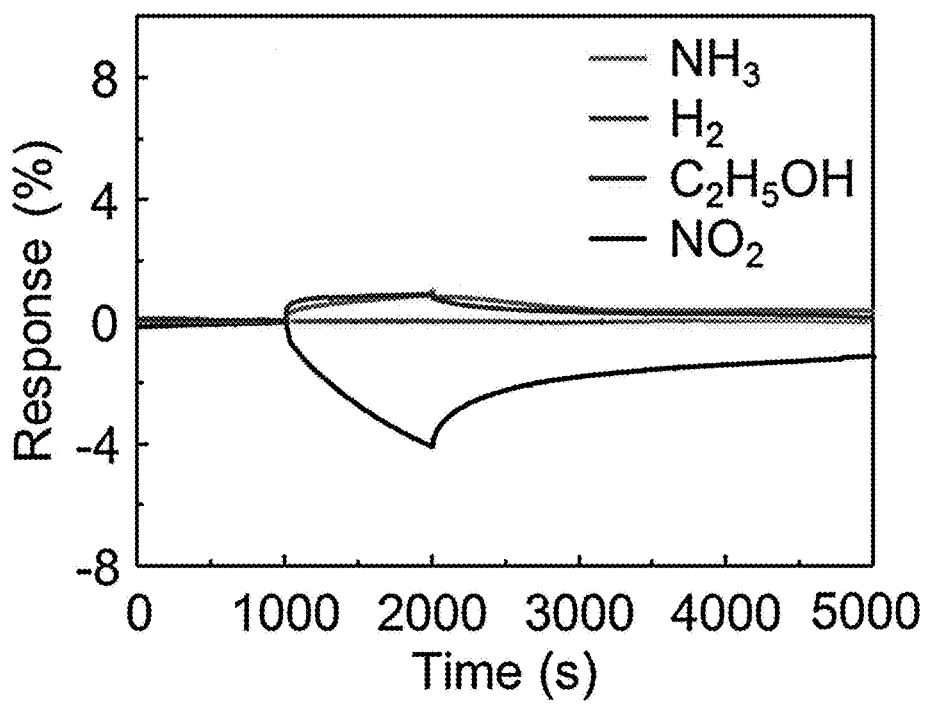
FIGS. 6A-6D show the gas-sensing characteristics of a flexible sensor array according to an exemplary embodiment of the present disclosure depending on surface decoration.
Figure 6B:
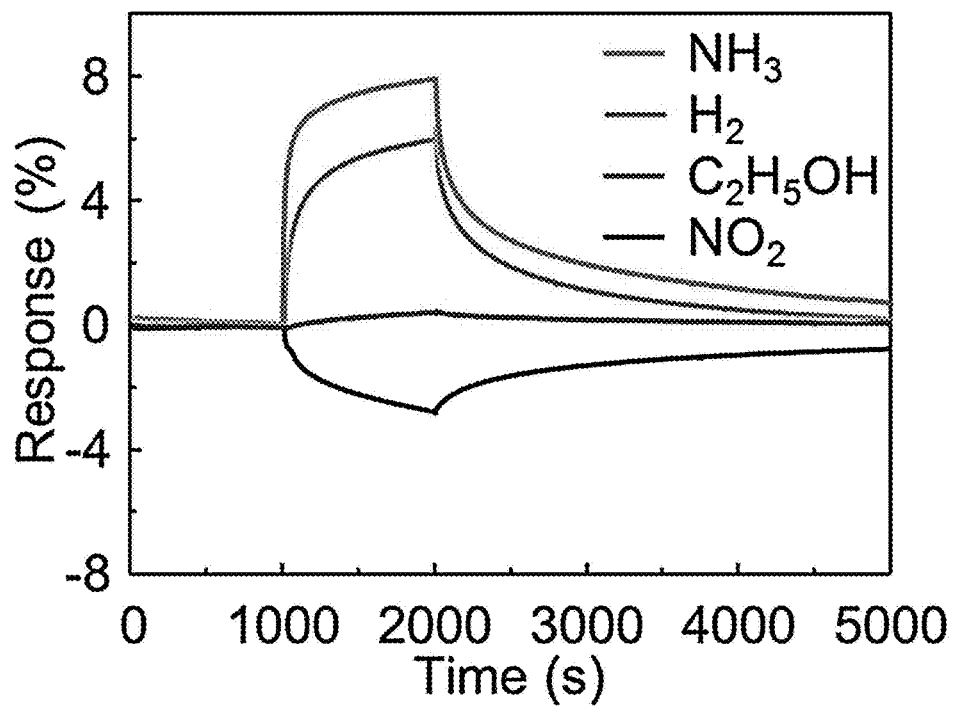
Figure 6C:
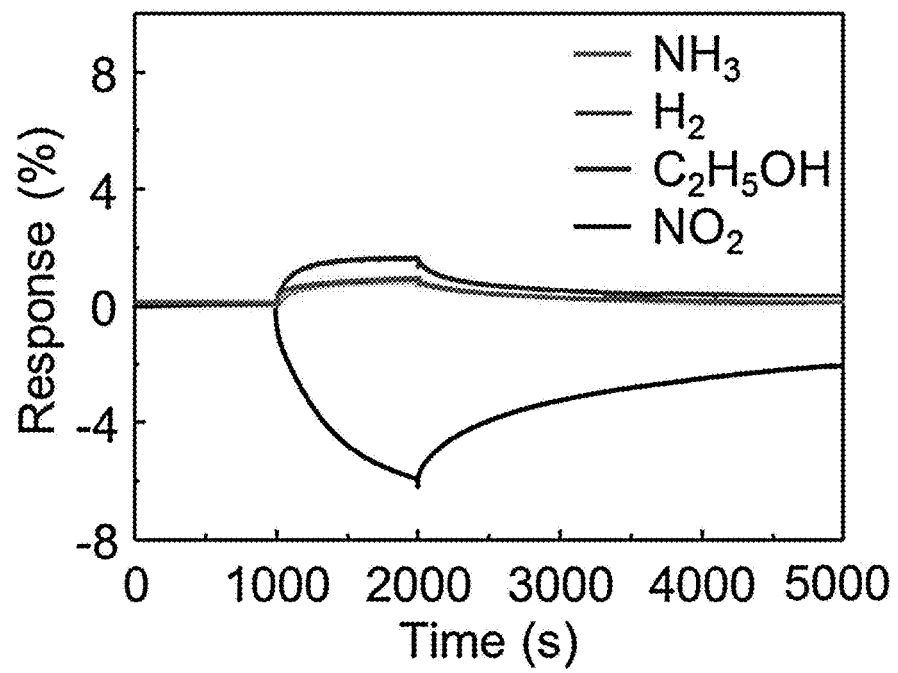
Figure 6D:
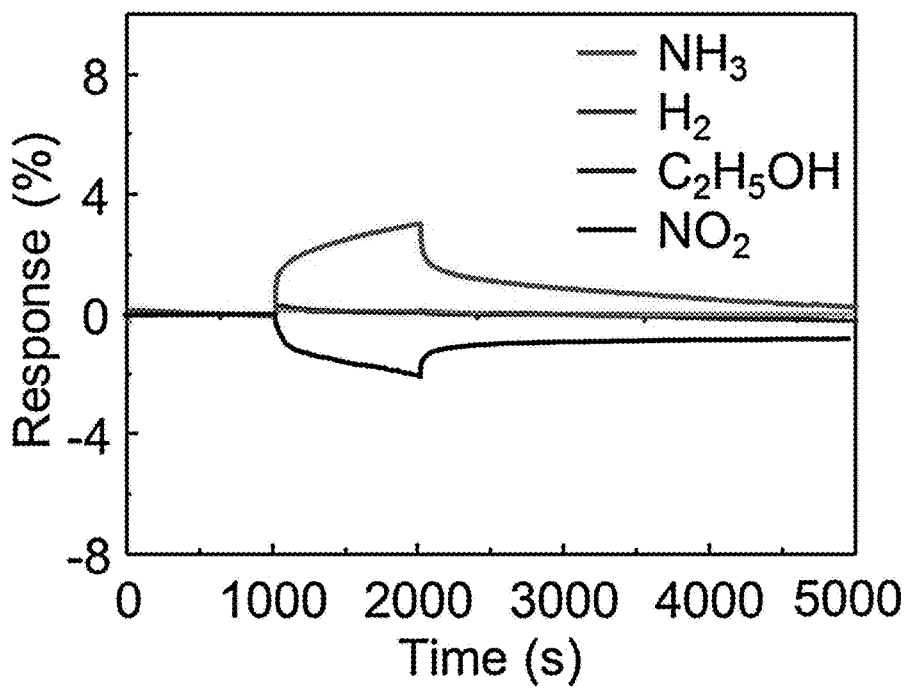
Figure 7A:
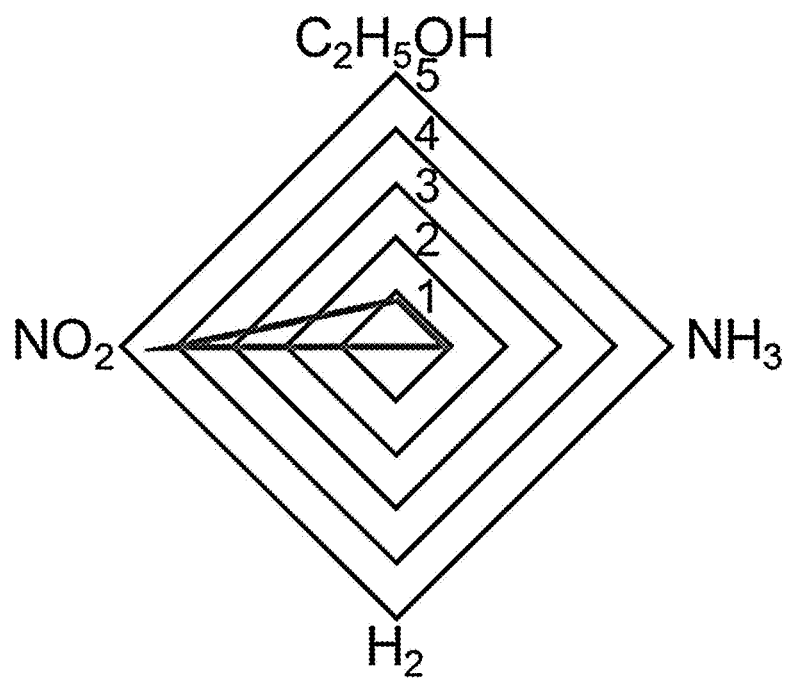
FIGS. 7A-7D show the gas-sensing pattern of a flexible sensor array according to an exemplary embodiment of the present disclosure depending on surface decoration.
Figure 7B:
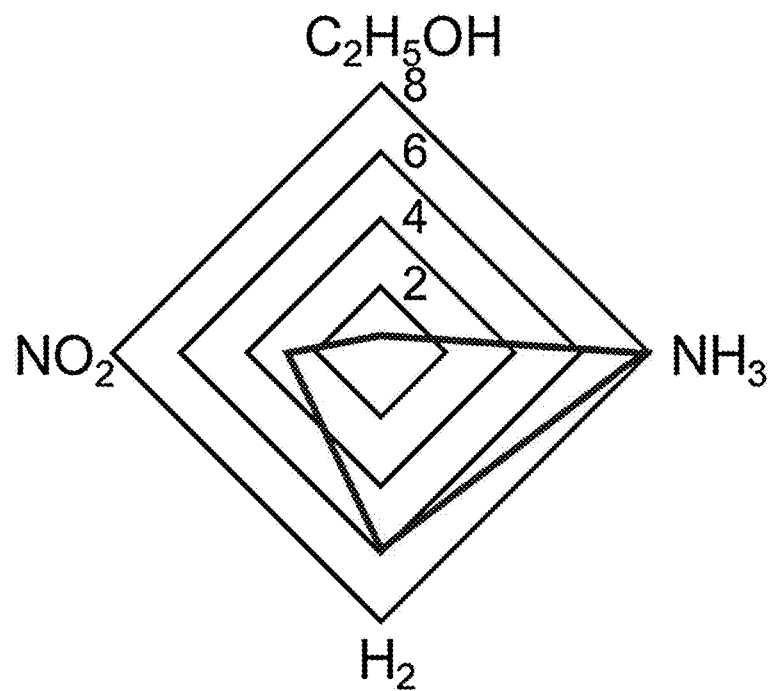
Figure 7C:
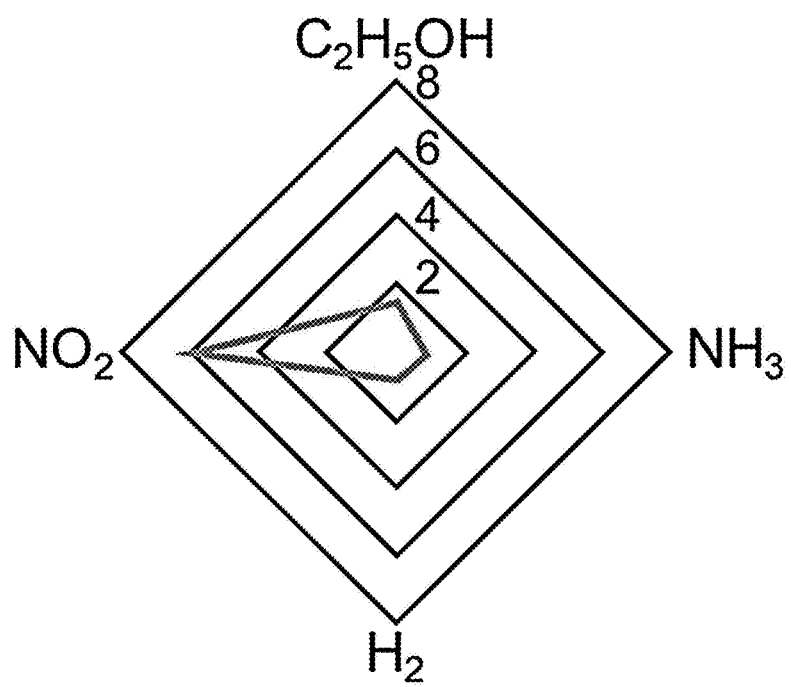
Figure 7D:
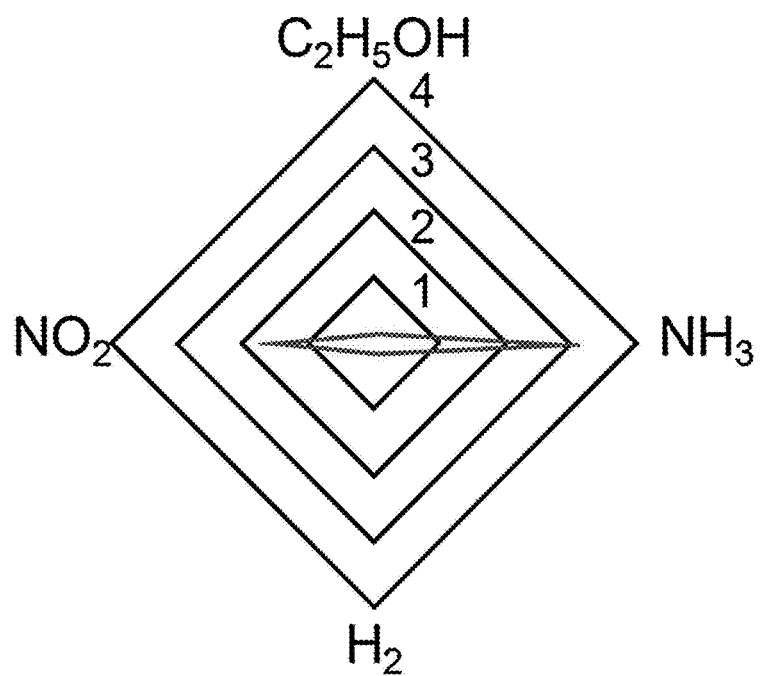

Test Example 1: Analysis of Sensitivity and Temperature of Flexible Graphene Gas Sensors with or without Surface Decoration Depending on Voltage For the gold (Au) surface-decorated flexible graphene gas sensor and the graphene gas sensor with no surface decoration manufactured in Example 1, a bias voltage of 1-60 V was applied for self-activation and the change in $H_2$ gas sensitivity and temperature depending on resistance was analyzed. The result is shown in FIGS. 5A and 5B. As shown in FIG. 5A, when 500 ppm of $H_2$ gas was supplied (about 2500 s), the flexible graphene gas sensor surface-decorated with gold (Au) nanoparticles showed superior $H_2$ gas sensing. When the supply of $H_2$ gas was stopped (about 3800s), the $H_2$ gas sensing ability decreased gradually. Also, as shown in FIG. 5b, both the gold (Au) surface-decorated flexible graphene gas sensor and the graphene gas sensor with no surface decoration showed rapid increase in temperature as the applied voltage was increased. Because the sensitivity is increased with temperature due to the change in resistance, it can be seen that temperature needs to be increased for gas sensing. The graphene gas sensor provided by the present disclosure can self-heat when an external voltage is applied even without an additional electrode. Therefore, a flexible graphene gas sensor with high sensitivity can be manufactured economically.

Test Example 2: Analysis of Gas-Sensing Characteristics, Gas-Sensing Pattern and Selectivity of Flexible Graphene Gas Sensor Array Depending on Surface Decoration For the flexible graphene gas sensors having a plurality of surface decorations manufactured in Example 2, a bias voltage of 1-60 V was applied for self-activation and NH$_3$, H$_2$, C$_2$H$_5$OH and NO$_2$ gas-sensing characteristics, gas-sensing pattern and selectivity were analyzed at room temperature. The result is shown in FIGS. 6a-6d, 7a-7d and 8.

FIGS. 6A-6D show the gas-sensing characteristics of the flexible graphene gas sensor arrays with no surface decoration, platinum (Pt) decoration, gold (Au) decoration and silver (Ag) decoration, respectively. FIGS. 7A-7D show the gas-sensing pattern of the flexible graphene gas sensor arrays with no surface decoration, platinum (Pt) decoration, gold (Au) decoration and silver (Ag) decoration, respectively. As shown in FIGS. 6A-6D and 7A-7D, for the gas sensor patterned only with graphene, the sensitivity for NO$_2$ was the best and the sensing of C$_2$H$_5$OH and NH$_3$ was possible. For the gas sensor surface-decorated with platinum (Pt), the sensitivity for NH$_3$ and H$_2$ was the best and the sensing of NO$_2$ was possible. For the gas sensor surface-decorated with gold (Au), the sensitivity for NO$_2$ was the best and the sensing of C$_2$H$_5$OH and H$_2$ was possible. The sensitivity for NH$_3$ and NO$_2$ was the best when the gas sensor was surface-decorated with silver (Ag). Therefore, if the gas sensor array is configured as described above, the reaction sensitivity and accuracy of sensing for different gases can be further improved.

Figure 8:
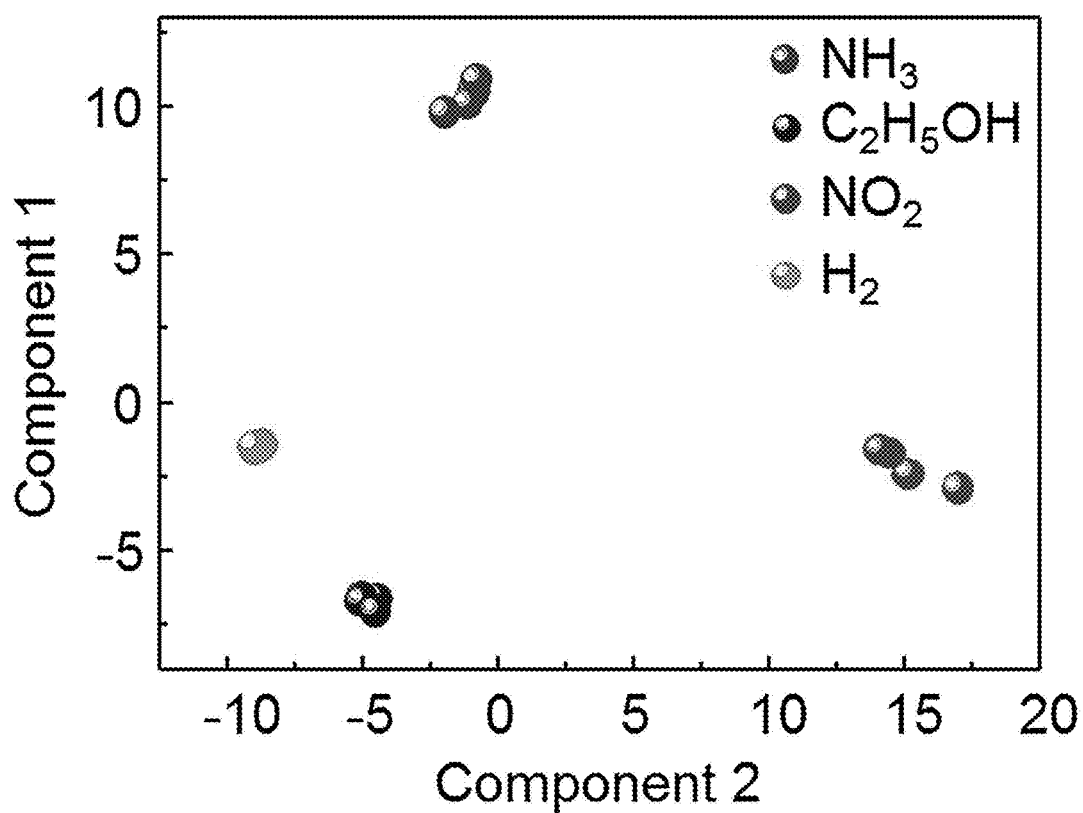
FIG. 8 shows a result of analyzing the gas-sensing characteristics of a flexible sensor array according to an exemplary embodiment of the present disclosure by PCA.

FIG. 8 shows a result of analyzing the gas-sensing characteristics of a flexible sensor array according to an exemplary embodiment of the present disclosure by principal component analysis (PCA). Referring to FIG. 8, it can be seen that each of the flexible graphene gas sensor arrays without surface decoration and with platinum (Pt) decoration, gold (Au) decoration and silver (Ag) decoration shows distinct gas-sensing characteristics, suggesting their high selectivity. Accordingly, the present disclosure provides a flexible graphene gas sensor array with high sensitivity for specific gases. Because the gas sensor array can be manufactured to be transparent due to the material characteristics of the flexible substrate, it can be utilized in wide applications including Internet of things, smart sensors, mobile phones, displays, automobiles, etc.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. A method for manufacturing a surface-decorated flexible graphene self-heating gas sensor array, comprising:
   a step of forming a graphene layer on a substrate;
   a step of forming a pattern of the graphene, the pattern comprising:
      a first graphene section;
      a second graphene section;
      a gap between the first and second graphene sections; and
      a connecting graphene section traversing the gap and connecting the first and second graphene sections;
   a step of coating a flexible substrate precursor solution on the patterned graphene layer and curing the precursor solution to form a flexible substrate;
   a step of removing the substrate;
   a step of placing a surface-decoration mask on the flexible substrate having the patterned graphene formed thereon; and
   a step of decorating, using the surface-decoration mask, the connecting graphene section with metal nanoparticles.

2. The method for manufacturing a flexible graphene self-heating gas sensor array of claim 1, wherein the step of forming the pattern of the graphene comprises a step of forming a micro-pattern or nano-pattern through a photolithography or e-beam lithography process, wherein the first graphene section and second graphene section are each in a shape of a right triangle, and wherein hypotenuses of the first and second graphene sections face each other and are parallel.

3. The method for manufacturing a flexible graphene self-heating gas sensor array of claim 1, wherein the substrate is a metal substrate comprising a transition metal.

4. The method for manufacturing a flexible graphene self-heating gas sensor array of claim 3, wherein the substrate is a metal substrate comprising copper or nickel.

5. The method for manufacturing a flexible graphene self-heating gas sensor array of claim 4, wherein the step of removing the substrate comprises a step of removing the metal substrate comprising copper or nickel with ammonium persulfate, an aqueous FeCl$_3$ solution or a strong acid.

6. The method for manufacturing a flexible graphene self-heating gas sensor array of claim 5, further comprising a thermal lamination step after the coating and curing of the flexible substrate.

7. The method for manufacturing a flexible graphene self-heating gas sensor array of claim 1, wherein the step of decorating with the metal nanoparticles comprise a step of depositing one or more metal nanoparticle(s) using an e-beam evaporator.

8. The method for manufacturing a flexible graphene self-heating gas sensor array of claim 1, wherein the metal nanoparticle is one or more selected from the group consisting of gold (Au), platinum (Pt), silver (Ag), tin (Sn), indium (In), nickel (Ni), copper (Cu), cobalt (Co), and chromium (Cr).

9. The method for manufacturing a flexible graphene self-heating gas sensor array of claim 1, wherein the flexible substrate is formed of a transparent material selected from the group consisting of polyimide (PI), acryl, polycarbonate, polyethylene terephthalate (PET), and polyethersulfone (PES).

10. A method for manufacturing a surface-decorated flexible graphene self-heating gas sensor array, comprising:
   a step of forming a graphene layer on a substrate;
   a step of forming a pattern of the graphene, the pattern comprising:
      a first graphene section;
      a second graphene section;
      a gap between the first and second graphene sections; and
      a connecting graphene section traversing the gap and connecting the first and second graphene sections;
   a step of coating a flexible substrate on the patterned graphene layer;
   a step of laminating a thermal lamination film using a thermal laminator;
   a step of removing the substrate;

a step of placing a surface-decoration mask on the flexible substrate having the patterned graphene formed thereon; and a step of decorating, using the surface-decoration mask, the connecting graphene section with metal nanoparticles using an e-beam evaporator.

11. The method for manufacturing a flexible graphene self-heating gas sensor array of claim 10, wherein the step of forming the pattern of the graphene comprises a step of forming a micro-pattern or nano-pattern through a photolithography or e-beam lithography process, wherein the first graphene section and second graphene section are each in a shape of a right triangle, and wherein hypotenuses of the first and second graphene sections face each other and are parallel.

12. The method for manufacturing a flexible graphene self-heating gas sensor array of claim 10, wherein the substrate is a metal substrate comprising a transition metal.

13. The method for manufacturing a flexible graphene self-heating gas sensor array of claim 12, wherein the substrate is a metal substrate comprising copper or nickel.

14. The method for manufacturing a flexible graphene self-heating gas sensor array of claim 13, wherein the step of removing the substrate comprises a step of removing the metal substrate comprising copper or nickel with ammonium persulfate, an aqueous $FeCl_3$ solution or a strong acid.

15. The method for manufacturing a flexible graphene self-heating gas sensor array of claim 10, wherein the metal nanoparticle is one or more selected from the group consisting of gold (Au), platinum (Pt), silver (Ag), tin (Sn), indium (In), nickel (Ni), copper (Cu), cobalt (Co), and chromium (Cr).

16. The method for manufacturing a flexible graphene self-heating gas sensor array of claim 10, wherein the flexible substrate is formed of a transparent material selected from the group consisting of polyimide (PI), acryl, polycarbonate, polyethylene terephthalate (PET), and polyethersulfone (PES).

* * * * *